US008080520B2

(12) United States Patent
Venkataraman et al.

(10) Patent No.: US 8,080,520 B2
(45) Date of Patent: *Dec. 20, 2011

(54) COMPOSITION AND METHOD FOR TREATING IRON DEFICIENCY ANEMIA

(76) Inventors: Bala Venkataraman, Alpharetta, GA (US); Michael Guthrie, Grand Junction, CO (US)

( * ) Notice: Subject to any disclaimer, the term of this patent is extended or adjusted under 35 U.S.C. 154(b) by 333 days.

This patent is subject to a terminal disclaimer.

(21) Appl. No.: 12/506,139

(22) Filed: Jul. 20, 2009

(65) Prior Publication Data
US 2009/0281021 A1 Nov. 12, 2009

Related U.S. Application Data

(63) Continuation of application No. 11/230,042, filed on Sep. 19, 2005, now Pat. No. 7,585,527.

(51) Int. Cl.
*A61K 38/00* (2006.01)
*A61K 38/41* (2006.01)
*A61K 38/42* (2006.01)
*A61K 33/26* (2006.01)
*C07K 14/805* (2006.01)

(52) U.S. Cl. ........... 514/5.4; 514/5.5; 514/502; 530/385
(58) Field of Classification Search .................. None
See application file for complete search history.

(56) References Cited

U.S. PATENT DOCUMENTS

| | | | |
|---|---|---|---|
| 3,821,192 | A | 6/1974 | Montgomery et al. |
| 4,411,915 | A | 10/1983 | Eriksson |
| 5,217,998 | A | 6/1993 | Hedlund et al. |
| 5,631,219 | A | 5/1997 | Rosenthal et al. |
| 5,919,755 | A | 7/1999 | Kangassaho et al. |
| 6,197,329 | B1 | 3/2001 | Hermelin et al. |
| 6,258,846 | B1 | 7/2001 | Hermelin et al. |
| 6,569,857 | B1 | 5/2003 | Hermelin et al. |
| 6,576,666 | B2 | 6/2003 | Hermelin et al. |
| 7,112,609 | B2 | 9/2006 | Hermelin et al. |
| 7,585,527 | B2 | 9/2009 | Venkataraman et al. |
| 2003/0170344 | A1 | 9/2003 | Russell et al. |
| 2003/0190355 | A1 | 10/2003 | Hermelin et al. |
| 2004/0176344 | A1 | 9/2004 | Rooney |
| 2004/0254155 | A1 | 12/2004 | Bommer |
| 2005/0020487 | A1 | 1/2005 | Klaus et al. |
| 2005/0037065 | A1 | 2/2005 | Kirschner et al. |

FOREIGN PATENT DOCUMENTS

| | | |
|---|---|---|
| CA | 2663584 A1 | 3/2007 |
| WO | 9313783 A1 | 7/1993 |
| WO | 2007/003575 A2 | 3/2007 |
| WO | 2007/035757 A3 | 3/2007 |

OTHER PUBLICATIONS

Order of Dismissal Pursuant to Fed. R. Civ. P. 4(m), issued in *Seton Pharmaceuticals, LLC* v. *Alaven Pharmaceutical LLC*, U.S.D.C. NJ, Civil Action No. 3:10-cv-02518-JAP, dated Nov. 29, 2010.

Nissenson et al. "Clinical Evaluation of Heme Iron Polypeptide: Sustaining a Response to rHuEPO in Hemodialysis Patients" American Journal of Kidney Diseases, vol. 42, No. 2 (Aug.), 2003: pp. 325-330.
Beard, John L. "Effectiveness and Strategies of Iron Supplementation During Pregnancy" American Journal for Clinical Nutrition; 71 (suppl): (2000), pp. 1288S-1294S.
Seligman et al. "Clinical Studies of Hip: An Oral Heme-Iron Product" Elsevier Science, Inc.—Nutrition Research, vol. 20, No. 9 (2000), pp. 1279-1285.
Roughead et al. "Initial Uptake and Absorption of Nonheme Iron and Absorption of Heme Iron In Humans are Unaffected by the Addition of Calcium as Cheese to a Meal With High Iron Bioavailability" American Journal for Clinical Nutrition, (2002) 76: pp. 419-425.
Roughead et al. "Adaptation in Iron Absorption: Iron Supplementation Reduces Nonheme-Iron but not Heme-Iron Absorption from Food" American Journal for Clinical Nutrition, (2000) 72: pp. 982-989.
Bereman et al. "The Structure, Size and Solution Chemistry of a Polysaccharide Iron Complex" Inorganica Chimica Acta, 155 (1989) pp. 183-189.
Beard, et al. "Iron Status and Exercise" American Journal for Clinical Nutrition, (2000) 72 (suppl): 594S-597S.
Gräsbeck et al. "An Intestinal Receptor for Heme" Scandinavian Journal of Hemotology (1979) vol. 23, pp. 5-9.
Uzel et al. "Absorption of Heme Iron" Seminars in Hematology, (Jan. 1998) vol. 35, No. 1, pp. 27-34.
Pizarro et al. "Heme-Iron Absorption is Saturable by Heme-Iron Dose in Women" Human Nutrition and Metabolism Research Communication, American Society for Nutritional Sciences (2003), pp. 2214-2217, vol. 133.
Ito et al., "Effect of Heme-Iron Food (BIOION 150) On Iron Deficiency and Iron Deficiency Anemia", Japanese Journal of Clinical Nutrition, vol. 78, No. 7, (1991), pp. 841-846.
Hallberg et al., "Iron Absorption from the Whole Diet in Men: How Effective is the Regulation of Iron Absorption?", The American Journal of Clinical Nutrition, (1997), pp. 347-356.
Hallberg et al., "Effect of Ascorbic Acid on Iron Absorption From Different Types of Meals. Studies with Ascorbic-Acid-Rich Foods and Synthetic Ascorbic Acid Given in Different Amounts with Different Meals", Human Nutrition-Applied Nutrition, (Apr. 1986), pp. 97-113, (Pubmed abstract).
Sharma et al., "Effect of Omeprazole on Oral Iron Replacement in Patients with Iron Deficiency Anemia", Southern Medical Journal, vol. 97, No. 9, (Sep. 2004), pp. 887-889.
Ekman et al., "Comparative Absorption of Ferrous and Heme-Iron with Meals in Normal and Iron Deficient Subjects", Z Ernährungswissenschaft, vol. 32, (1993), pp. 67-70.
Sandstad et al.,"Selective Iron Supplementation Based on Serum Ferritin Values Early in Pregnancy: Are the Norwegian Recommendations Satisfactory?", Acta Obstetricia et Gynecoligica Scandinavica, vol. 82, (2003), pp. 537-542.
Eskeland et al., "Iron Supplementation in Pregnancy: Is Less Enough?", Acta Obstetricia et Gynecoligica Scandinavica, vol. 76, (1997), pp. 822-828.

(Continued)

*Primary Examiner* — Marsha Tsay
(74) *Attorney, Agent, or Firm* — Thompson Hine LLP

(57) ABSTRACT

A composition comprising heme iron and/or heme iron polypeptide in combination with ionic iron(s) and/or chelated iron(s). Administration of effective dosages of the present composition provides a method for treating and/or preventing iron deficiency anemia, and the physiological, biochemical, morphological, and behavioral manifestations symptomatic of same.

8 Claims, No Drawings

OTHER PUBLICATIONS

Koren et al., "Compliance with Prenatal Vitamins", Canadian Family Physician, vol. 52, (Nov. 2006), pp. 1392-1393.

Shayeghi et al., "Identificaiton of an Intestinal Heme Transporter" Cell, vol. 122, (Sep. 9, 2005), pp. 789-801.

Nancy C. Andrews, M.D., Ph.D., "Understanding Heme Transport", The New England Journal of Medicine, 353:23, (Dec. 8, 2005), pp. 2508-2509.

Nancy C. Andrews, M.D., Ph.D., "Disorders of Iron Metabolism", The New England Journal of Medicine, vol. 341, No. 26, (Dec. 23, 1999), pp. 1986-1996.

Piccinni et al., "Therapeutic Effectiveness of an Iron-Polysaccharide Complex in Comparison with Iron Fumarate in the Treatment of Iron Deficiency Anaemias", Pan Medical, vol. 24, (1982), pp. 213-220.

Heffernan, et al., "Polysaccharide-Iron Complex Use in Chronic Dialysis Patients Receiving Erythropoietin", (1991), pp. 1-22.

Newton et al., Prohylaxis of Iron Deficiency Anaemia of Prematurity, Clinical Trials Journal, vol. 17, No. 3, (1980), pp. 106-111.

Ghaddar et al., "Evaluation of the Ability of Heme Iron Polypeptide to Sustain Response to rHuEPO in Peritoneal Dialysis Patients: A Prospective Clinical Evaluation", abstract presented at NFK, Apr. 7, 2003, Dallas, TX.

Casiday, R., et al., "Hemoglobin and the Heme Group: Metal Complexes in the Blood for Oxygen Transport" Washington University, Department of Chemistry, Jun. 21, 2007 (tutorial) 15 pages.

Colorado Biolabs, Inc.,"Proferrin® ES (heme iron polypeptide)— Product Ordering Information" pamphlet, Colorado Biolabs, Inc., Cozad, Nebraska, Mar. 2005.

Colorado Biolabs, Inc., "Proferrin® Forte (heme iron polypeptide with folic acid)" Product Literature; Colorado Biolabs, Inc., Cozad, Nebraska, Mar. 2005.

Colorado Biolabs, Inc.,"Proferrin® Forte (heme iron polypeptide with folic acid-medical food)" www.coloradobiolabs.com/ProferrinForte/default.aspx, Dec. 31, 2005.

Colorado Biolabs, Inc., Proferrin® (heme iron polypeptide), www.coloradobiolabs.com/default.aspx, Dec. 31, 2005.

Frykman, E. et al., "Side Effects of Iron Supplements In Blood Donors: Superior Tolerance of Heme Iron", [Pub Med] Journal of Laboratory and Clinical Medicine, Apr. 1994, 561-4, (abstract).

[No author named] Research Database—International Updates Pregnancy / Menstruation Issue 30, www.positivehealth.com/permit/updates/redpreg.htm [date unknown] web accessed date Apr. 25, 2006.

[No author named] Hemofer, US Patent and Trademark Office Trademark Electronic Search System (TESS) www.uspto.gov [date unknown] web accessed date Apr. 25, 2006.

[No author named] Hemofer-B-Complex, www.comed.be/paarden/hemofere.htm [Date unknown] web accessed date Apr. 25, 2006.

[No author ] "Hemoglobin" Wikipedia, http://en.wikipedia.org/wiki/Hemoglobin web accessed date Oct. 17, 2007.

Britannica Online Encyclopedia—definition of partial acid hydrolysis (2009): 1 page.

MacDougal et al., "A randomized controlled study of iron supplementation in patients treated with erythropoietin" Kid Internat 1996; 50(5): 1694-1699.

Auerback et al., "A randomized trial of three iron dextan infusion methods for anemia in EPO-treated dialysis patients" Am J Kid Dis 1998; 31(1): 81-86.

[No author named] "A Study of the preventative effects of a highly absorbable iron supplement on an anemia" The Society of Physical Fitness, Nutrition and Immunology 1996; 6(1), pp. 47-56.

Conrad et al., "Absorption of hemoglobin iron" Am J Physio 1996; 211: 1123-1130.

Herzog C., "Acute myocardial infarction in patients with end-stage renal disease" Kid Int Suppl 1999; 71: S130-3.

Chowdhury B, Chandra R., "Biological and health implications of toxic heavy metal and essential trace element interactions" Prog Food Nutr Sci 1987; 11(1): 57-113.

Wu W, Rathore S, Wang Y, Radford M, Krumhoz H;"Blood Transfusion in elderly patients with acute myocardial infarction" New England Journal of Medicine, Oct 15, 2001; 345(17): 1230-1236.

Foley et al., "Cardiac Function and Hematocrit Level" Am. J. of Kid. Dis. 1995; 25(4) Suppl 1, pp. S3-S7.

Litovitz T., Manoguerra A., "Comparison of pediatric poisoning hazards: An analysis of 3.8 million exposure incidents" American Association of Poison Control Centers Pediatrics, Jun. 1992; 89 (6 Pt 1): 999-1006.

Gasche C., "Complications of inflammatory bowel disease" Hepatogastroenterology, Jan.-Feb. 2000; 47(31): 49-56.

Skikne BS, Cook JD, "Effect of enhance erythropoiesis on iron absorption" J. Lab Clin Med. 1992; 120(5):746-751.

McCord, J., "Effects of Positive Iron Status at a Cellular Level" Nutrition Reviews 1996; 54 (3): 85-88.

Monsen et al., "Estimation of available dietary iron" Am. J. of Clin. Nutr. 1978; 31: 134-141.

Monsen et al., "Food Iron Absorption in Human Subjects IV—The Effect of calcium and phosphate on the absorption of non-heme iron" Am. J. Of Clin. Nutr. 1976; 29: 1142-1148.

Björn-Rasmussen E, Hallberg L, Isaakson B, Arvidsson B., "Food Iron Absorption in Man: Application of the two-pool extrinsic tag method to measure heme and nonheme iron absorption form the whole diet" J Clin Invest 1974; 53: 247-255.

Fischer, H., "Hemin" Organic Synthesis; Collective vol. 3 1955, p. 442.

Ganz T., "Hepcidin, a key regulator of iron metabolism and mediator of anemia of inflammation" Blood, Aug. 1, 2003 102 (3): 783-788.

Novey, Haydik, & Vaziri, "Immunologic studies of anaphylaxis to iron dextran in patients on renal dialysis" Annals of Allergy 1994; 73(2): 224-228.

Ambrosio et al., "Improvement of postischemic myocardial function and metabolism induced by administration of desferrioxamine at the time of reflow: the role of iron in the pathogenesis of reperfusion injury" Circulation 1987; 76(4): 906-915.

Raffin SB, Woo CH, Roost KT, et al., "Intestinal Absorption of Hemoglobin Iron-heme cleaved by Mucosal Heme Oxygenase" J. Of Clin. Invest. 1974; 54: 1344-1352.

Silverberg et al., "Intravenous iron supplementation for the treatment of the anemia of moderate to severe chronic renal failure patients not receiving dialysis" Am J Kid Dis 1996; 27(2): 234-238.

Umbriet J, Conrad M, Moore E, Latour L., "Iron absorption and cellular transport: the Mobilferrin/Paraferritin paradigm" Seminars in Hematology 1998; 35(1): 13-26.

Turnbull A et al., "Iron Absorption: The Absorption of hemoglobin iron" J. Of Clin Invest 1962; 41: 1897-1907.

van der Kraalj et al., "Iron Load Increases the Susceptibility of Rat Hearts to Oxygen Reperfusion Damage" Circulation 1988; 78(2): 442-449.

Watson A., "Iron Management During Treatment with Recombinant Human Erythropoietin in Chronic Renal Failure" J. of Clin Pharmacology 1993; 33: 1134-1138.

Fishbane S, Maesaka J., "Iron Management in End-Stage Renal Disease" Am. J. of Kid. Dis. 1997; 29(3): 319-333.

Monsen, ER., "Iron nutrition and absorption: Dietary factors which impact iron bioavailability" J. Am Diet Assoc. 1988; 88(7): 786-790.

Seifert A, Von Herrath D, Scheafer K., "Iron overlaod, but not treatment with desferrioxamine favours the development of septicemia in patients on maintenance hemodialysis" Q. J. Med Dec. 1987; 65(248): 1015-1024.

Araujo et al., "Iron Overload Augments the Development of Atheroscherotic Lesions in Rabbits" Arteriosclerosis, Thrombosis, and Vascular Biology 1995; 15 (8): 1172-1180.

McCord J., "Iron, Free Radicals, and Oxidative Injury" Seminars in Hematology 1998; 35(1): 5-12.

Drueke, TB et al., "Management of iron deficiency in renal anemia: guidelines for the optimal therapeutic approach in erythropoietin-treated patients" Clin. Nephrol 1997; 48(1):1-8.

Seligman et al., "Measurements of Iron Absorption form Prenatal Multivitamin-Mineral Supplements" Obstetrics and Gynecology 1983; 61(3): 356-362.

Tamura et al. "Methodology of the Everted Gut Assay for Iron Absorption and Estimation of Heme iron" J. of the Jap. Soc. of Nutr. And Food Science 1988; 41(6): 490-495.

Jacob, H., "Newly Recognized Causes of atheroschlerosis: The role of microorganisms and of vascular iron overload" J. of Lab. and Clin. Med. 1994; 123 (6): 808-816.

Goyer R., "Nutrition and metal toxicity" Am J Clin Nutr 1995; 61(3 Suppl): 646S-650S.

Linder M, Ph.D., "Nutritional Biochemistry And Metabolism: With Clinical Applications" Elsevier Publishers—New York 1987; pp. 149-197.

Donnelly et al., "Oral Iron Absorption in hemodialysis patients treated with erythropoietin" Clin. Invest. Med. 1991; 14 (4): 271-276.

Mavromatidis et al., "Serum Ferritin levels are increased in patients with acute renal failure" Clin Neph 1998; 49(5): 296-298.

Rybo G, Lennart S., "Side-effect studies of a new sustained release iron preparation" Scandinavian journal of Haematology 1971; 8: 257-264.

Nissenson A, Lindsay R, Swan S, Seligman P, Strobos J., "Sodium Ferric Gluconate Complex in sucrose is safe and effective in hemodialysis patients: North American Clinical Trial" Am J Kid Dis 1999; 33(3); 471-482.

Gräsbeck, et al., "Spectral and other stud-ies on the intestinal haem receptor of the pig" Biochem Biophys Acta 1982; 700: 137-142.

Scientific Working Group, "Summary of a report on assessment of the iron nutritional status of the United States population" Am J Clin Nutr 1985; 42: 1318-1330.

Chen H, Atteih ZK, Fox TC, McKie AT, Anderson GJ, and Vulpe CD., "Systemic regulation of hephaestin and IREG1 revealed in studies of genetic and nutritional iron deficiency" Blood, Sep. 2003 102 (5) : 1893-1899.

Van Jaarsveld et al., "The Effect of Desferal on Rat Heart Mitochondiral Function, Iron Content, and Xanthine Dehydrogenase/Oxygenase Conversion During Ischemic Reperfusion" Clinical Biochemistry 1990; 23, 509-513.

Kalender B, Mantlu B, Ersoz M, Kalkan A, Yilmaz A., "The Effects of Acute Phase proteins on serum albumin, transferring and haemoblobin in haemodialysis patients" Int. J. Of Clin Pract 2002, Sep.; 56(7): 505-508.

Kosiborod M, Smith GL, Radford MJ, Foody JM, Krumholz HM., "The Prognostic Importance of Anemia in Patients with Heart Failure" Am J Med 2003; 114(2): 112-119.

Bezwoda, Bothwell, et al., "The Relative dietary importance of haem and non-haem iron" South African Med. J. 1983; 64(14): 552-556.

Fishbane et al., "The Safety of Intravenous Iron Dextran in Hemodialysis Patients" Am. J. of Kid. Dis. 1996; 28(4): 529-534.

Lesnefsky E., "Tissue Iron overload and mechanisms of iron-catalyzed oxidative injury" Adv Exp Med Bio 1994; 366: 129-146.

Shils and Young, Modern Nutrition in Health and Disease (1988), Lea & Feiberger Publishers ⌐Philadelphia, 7 th Edition, pp. 193-226.

Suitor and Crowley Nutrition ⌐Principals and Application in Health Promotion, 2nd Ed. JB Lippincott & Co.—Philadelphia, pp. 41-58, 1984.

Hallberg, L., "Iron requirements and bioavailability of dietary iron.", Experientia Suppl. 1983; 44:223-44; PubMed Abstract.

Lynch, SR and Cook, JD., "Interaction of vitamin C and iron.", Ann N Y Acad Sci. 1980; 355:32-44; PubMed Abstract.

Gadsby et al., "A prospective study of nausea and vomiting during pregnancy", British Journal of General Practice,vol. 43, Jun. 1993, pp. 245-248.

Dreon et al., "Change in dietary saturated fat intake is correlated with change in mass of large low-density-lipoprotein particles in men" Am J Clin Nutr, vol. 67, 1998, pp. 828-836.

Lacroix et al., "Nausea and vomiting during pregnancy: A prospective study of its frequency, intensity, and patterns of change" Am J Obstet Gynecol, vol. 182, No. 4, Apr. 2000, pp. 931- 937.

Hudson et al., "Considerations for Optimal Iron Use for Anemia Due to Chronic Kidney Disease" Clinical Therapeutics, vol. 23, No. 10, 2001, pp. 1637-1671.

Szarfarc et al., "Relative effectiveness of iron bis-glycinate chelate (Ferrochel) and ferrous sulfate in the control of iron deficiency in pregnant women" Archivos Latinoamericanos de Nutricion, vol. 51 No. 1, 2001, pp. 42-47.

Acog Practice Bulletin, Clinical Management Guidelines for Obstetrician-Gynecologists, Nausea and Vomiting of Pregnancy, vol. 103, No. 4, Apr. 2004, pp. 803-815.

Somsook et al., "Interactions between iron(III) and sucrose, dextran, or starch in complexes", Carbohydrate Polymers, vol. 61, 2005, pp. 281-287.

Guzun-Cojocaru et al., "Effect on iron chelates on oil-water interface, stabilized by milk proteins: The role of phosphate groups and pH. Prediction of iron transfer from aqueous phase toward fat globule surface by changes of interfacial properties", Food Hydrocolloids, vol. 24, 2010, pp. 364-373.

Complaint with Jury Demand, Seton Pharmaceuticals, LLC v. Alaven Pharmaceutical LLC, U.S.D.C. NJ, Civil Action No. 3:10-cv-02518-JAP, dated May 17, 2010.

Form AO 120, Report on the filing or determination of an action regarding a patent or trademark, Seton Pharmaceuticals, LLC v. Alaven Pharmaceutical LLC, U.S.D.C. NJ, Civil Action No. 3:10-cv-02518-JAP, dated May 18, 2010.

Frykman, E., et al, Side effects of iron supplements in blood donors: Superior tolerance of heme iron, J Lab Clin Med 1994;123(4): 561-4.

Jewell, D. and Young, G., Interventions for nausea and vomiting in early pregnancy (Review), Cochrane 2007, Issue 2.

Jewell D, Young G. Interventions for nausea and vomiting in early pregnancy. Cochrane Database of Systematic Reviews 2003, Issue 4. (Reprinted and Published: The Cochrane Library, 2009; Issue 1).

Merck Manual, Anemia in Pregnancy (Nov. 2005), <http://www.merck.com/mmpe/sec18/ch261/ch261b.html>.

Hallberg, L., Bioavailability of Dietary Iron in Man, Ann. Rey. Nutr. 1981. 1:123-47.

Gordeuk, V., et al, Carbonyl Iron Therapy for Iron Deficiency Anemia, Blood 1986; 67(3):745-52.

Quinlan, J. and Hill, D., Nausea and Vomiting of Pregnancy, Am Fam Phy 2003; 68(1):121-8.

Centers for Disease Control and Prevention. Facts About Folic Acid (CDC Website, 2009), <http://www.cdc.gov/ncbddd/folicacid/about.html>.

Centers for Disease Control and Prevention. Birth Defects. (CDC Website, 2007); <http://web.archive.org/web/20071212181130m_1/www.cdc.gov/ncbddd/bd/default.htm>.

Centers for Disease Control and Prevention. Birth Defects. (CDC Website, 2010) <http://www.cdc.gov/ncbddd/bd/default.htm>.

Bishai R, Mazzotta P, Atanackovic G et al. Critical appraisal of drug therapy for nausea and vomiting of pregnancy: II. Efficacy and safety of diclectin (doxylamine-B6). Can J Clin Pharmacol 2000;7(3):138-43.

Centers for Disease Control and Prevention. Iron deficiency—United States, 1999-2000. MMWR 2002;51(40):897-9.

Viteri F, Berger J. Importance of prepregnancy and pregnancy iron status: can long-term iron and folic acid supplementation achieve desirable and safe status? Nutr Rev 2005;63(Suppl 12):65-76.

Scanlon KS, Yip R, Schieve LA, Cogswell ME. High and low hemoglobin levels during pregnancy: differential risks for preterm birth and small for gestational age. Obstet Gynecol 2000;96(5 Pt 1):741-8.

Tomashek KM, Ananth CV, Cogswell ME. Risk of stillbirth in relation to maternal haemoglobin concentration during pregnancy. Matern Child Nutr 2006;2(1):19-28.

Hamalainen H, Hakkarainen K, Heinonen S. Anaemia in the first but not in the second or third trimester is a risk factor for low birth weight. Clin Nutr 2003;22(3):271-5.

The Merck Manual. Sources, Functions and Effects of Vitamins. (2005); <http://www.merck.com/media/mmpe/pdf/Table_004-3.pdf>.

Lozoff B, Georgieff MK. Iron deficiency and brain development. Semin Pediatr Neurol 2006;13(3):158-65.

Cook J, Flowers C, Skikne B. The quantitative assessment of body iron. Blood 2003;101:3359-64.

Scholl TO, Hediger ML, Bendich A, Schall JI, Smith WK, Krueger PM. Use of multivitamin/mineral prenatal supplements: influence on the outcome of pregnancy. Am J Epidemiol 1997;146(2):134-41.

Peña-Rosas JP, Viteri FE. Effects of routine oral iron supplementation with or without folic acid for women during pregnancy. Cochrane Database of Systematic Reviews 2009, Issue 3.

Peña-Rosas JP, Viteri FE. Effects and safety of preventive oral iron or iron+folic acid supplementation for women during pregnancy. Cochrane Database of Systematic Reviews 2009, Issue 4.

March of Dimes. Choosing a multivitamin. Mar. Of Dimes (2007); <http://www.marchofdimes.com/pnhec/173_15354.asp>.

National Institute of Child Health & Human Development. Prenatal Care. (National Institute of Health Website 2006); <http://web.

archive.org/web/20061002065715/http://www.nichd.nih.gov/health/topics/Prenatal_Care.cfm>.

National Institute of Child Health & Human Development. Preconception Care. (National Institute of Health Website 2010); <http://www.nichd.nih.gov/health/topics/preconception_care.cfm>.

Smith C, Crowther C, Beilby J, Dandeaux J. The impact of nausea and vomiting on women: a burden of early pregnancy. Aust N Z J Obstet Gynaecol 2000;40(4):397-401.

Ahn E, Pairaudeau N, Pairaudeau N, Jr. et al. A randomized cross over trial of tolerability and compliance of a micronutrient supplement with low iron separated from calcium vs high iron combined with calcium in pregnant women. BMC Pregnancy Childbirth 2006;6:10.

Koren G, Pairaideau N. Compliance with prenatal vitamins. Patients with morning sickness sometimes find it difficult. Can Fam Physician 2006;52(11):1392-3.

Meltzer DI. Selections from current literature. Complementary therapies for nausea and vomiting in early pregnancy. Fam Pract 2000;17(6):570-3.Source: IMS Data.

Martek Biosciences Corporation, Columbia, MD. Your Diet, DHA and Omega 3 Fatty Acids. (Martek Biosciences Corporation Website, 2010); <http://www.lifesdha.com/Pregnant-and-Nursing-Women/About-lifesDHA-.aspx>.

McColl, K., Effect of Proton Pump Inhibitors on Vitamins and Iron, Am J Gastroenterol 2009; 104:S5-S9; doi: 10.1038/ajg.2009.45.

Calonge, N., et al, Clinical Guidelines: Folic Acid for the Prevention of Neural Tube Defects: U.S. Preventive Services Task Force Recommendation Statement, Ann Intern Med. 2009;150:626-631.

Hallberg, L., Iron requirements and bioavailability of dietary iron, Experientia Supp. 1983;44:223-44.

Lynch, S. R., Interaction of Iron with Other Nutrients, Nutrition Reviews, 1997. 55(4):102-10.

Naude, S., et. al., Iron Supplementation in Preterm Infants: A Study Comparing the Effect and Tolerance of a Fe2+ and a Nonionic FeIII Compound, J Clin Pharmacol, 2000; 40:1447-1451.

Gasche, C., et. al., Iron, anaemia, and inflammatory bowel diseases Gut 2004;53:1190-1197.

Ostrow, J. D. "Tests for Fecal Occult Blood" in Clinical Methods: The History, Physical, and Laboratory Examinations. Walker, H. K., et al, ed. Stoneham, MA: Butterworth Publishers; 1990: 489-91.

Pagewise, eSSortment, eSSortment.com, "Symptoms of iron deficiency" (2002); <http://www.essortment.com/all/irondeficiency_rchi.htm>.

Health Grades Inc., WrongDiagnosis.com, "Symptoms of Iron deficiency anemia" (2010); <http://www.wrongdiagnosis.com/i/iron_deficiency_anemia/symptoms.htm>.

Wikimedia Foundation, Inc., Wikipedia.org, "Iron deficiency (medicine)" (Page last modified Jan. 27, 2010); http://en.wikipedia.org/wiki/Iron_deficiency_(medicine).

Nissenson, A., et al., Heme-Iron Polypeptide Maintains Iron Stores in Hemodialysis Patients, Clinical Nephrology: Outcomes, Epidemiology, M2-0464(PS), A1199.

Kim, S., et al., Physicochemical Properties of Heme Iron Products in the Korean Market, J Med Food 2006; 9(2): 231-236.

Venkataraman, et al., PCTUS2006/036525, Written Opinion of the International Searching Authority; Apr. 9, 2007.

COMPOSITION AND METHOD FOR TREATING IRON DEFICIENCY ANEMIA

PRIORITY CLAIM TO RELATED APPLICATIONS

To the fullest extent permitted by law, the present continuation patent application claims priority to and the full benefit of non-provisional patent application entitled "Composition and Method for Treating Iron Deficiency Anemia", filed on Sep. 19, 2005, having assigned Ser. No. 11/230,042.

TECHNICAL FIELD

The present invention relates generally to nutritional supplements and disease treatment, and more specifically to a composition and method for treating iron deficiency anemia.

BACKGROUND OF THE INVENTION

In the human body, iron is essential for the implementation and maintenance of several vital cellular functions and biosynthetic processes, including oxygen transport capabilities, aerobic cellular activity, intracellular electron transport, and integral enzymatic reactions within body tissue. Unfortunately, as a combined result of various socioeconomic conditions, environmental factors, genetic predispositions, and the collective dietary habits amongst the general populace, iron deficiency is the most common known form of nutritional deficiency amongst humans.

Of significant prevalence, especially amongst children and women (i.e., particularly pregnant women and/or women of childbearing age), is iron deficiency anemia, a condition defined by a gross reduction in overall iron levels in the red blood cells and, thus, a decline in hemoglobin synthesis, the molecule ultimately responsible for the transport and distribution of oxygen from the lungs to tissues of the body. Indeed, in pregnant women, iron deficiency increases both the risk of pre-term delivery and/or delivery of a low-birthweight baby, whereas with children, iron deficiency anemia may cause developmental delays, behavioral disturbances, altered growth patterns, and increased infections. Still other manifestations symptomatic of iron deficiency anemia may include pale skin tone or color, headaches, extreme fatigue, light-headedness, glossitis (swelling of the tongue), koilonychias (spoon nails), and other overt, albeit extreme, behavioral disturbances, such as the consumption of dirt or clay (pica or geophagia), or the abnormal consumption of ice (pagophagia).

Accordingly, the maintenance, or bioavailability, of nutritionally adequate iron levels is largely a collective function of the composition of food consumed, the quantity and chemical form of iron contained therein, and the presence of food items that either promote or inhibit iron absorption. Specifically, iron is absorbed as either a heme iron (an intact metalloporphyrin ring), or nonheme iron (ionic iron). Heme iron, however, which is principally found in meat as hemoglobin or myoglobin, is more readily and effectively absorbed than nonheme iron and, thus, provides a significantly greater dietary source of iron than nonheme iron. Additionally, food items such as bran, wheat, soy and other cellulosic products, which seemingly have no influence on heme iron absorption, tend to appreciably inhibit nonheme iron absorption; thus, exposing vegetarians to a relatively greater risk of developing an iron deficiency.

In fact, as professed by the American Society for Clinical Nutrition, approximately 5%-35% of heme iron is absorbed from a single meal, whereas nonheme iron absorption from a single meal can range from approximately 2% to 20%, depending on the iron status of the individual and the ratio of enhancers and promoters in the diet. Accordingly, although heme iron constitutes only approximately 10% of dietary iron intake, heme iron may provide up to one-third of overall absorbed dietary iron. Consequently, inadequate consumption of foods high in heme iron content, especially during periods of increased iron demand (i.e., gestational and/or lactational periods), deprives the body of a considerable percentage of necessary dietary iron. Unfortunately, whether due to staunch dietary habits or beliefs, or the unavailability of certain foods due to prevailing socioeconomic and/or geographic conditions, the consumption of foods low or deficient in heme iron content, or the strict consumption of nonheme iron foods, will likely result in iron deficiency anemia.

Accordingly, as an alternative to radical dietary adjustment, iron supplements have traditionally offered a more subtle, therapeutic approach to the treatment of iron deficiency. However, the efficacy of supplement intervention (i.e., total effective iron absorption) is dependent upon a number of factors, the most of germane of which is the composition of the supplement and the total iron dosage.

That is, various iron supplements are typically prescribed in doses containing between 40 mg and 150 mg of elemental iron per day, wherein a higher dosage of iron results in greater overall absorption. However, a high dose of iron as a dietary supplement (or fortificant) is not without consequence. Indeed, many existing iron supplements cause distressing side effects, such as nausea, diarrhea, constipation and/or cramping; thus, resulting in patient non-compliance with the prescribed supplement regimen. Further, it has been strongly suggested that high single doses of iron may contribute to the elevated formation of highly reactive oxygen radicals and, thus, promote various pathogenic processes, such as cardiovascular disease.

Still other clinically-administered iron supplement preparations that contain iron salts, such as ferrous sulfate, (hydrated) ferrous gluconate, or ferrous fumarate, as the primary iron source, may actually provide less iron than otherwise expected. Specifically, although inconsequential to heme iron absorption, dietary supplementation with such ferrous salts effectively reduces nonheme iron absorption and, thus, offers a counter-intuitive approach to individuals whose already limited iron intakes are dependent upon a diet high in nonheme iron content (i.e., vegetarians, indigents, etc.).

Therefore, it is readily apparent that there is a need for a composition and method for treating iron deficiency anemia, wherein the composition accounts for dietary inconsistencies across the broad spectrum of patient demographic, and further reduces, if not eliminates, the side effects associated with traditional iron supplements; thereby, increasing overall patient compliance. Accordingly, the composition of the present invention proffers such results through the combination of heme iron and/or heme iron polypeptide with ionic irons (i.e., iron salts) and/or chelated irons, wherein the combination provides a synergistic effect that substantially reduces the prescribed iron dosage, yet significantly increases overall iron absorption. There is a further need for such a composition that offers additional vitamins and minerals in conjunction with the prescribed iron content.

BRIEF SUMMARY OF THE INVENTION

Briefly described, in a preferred embodiment, the present invention overcomes the above-mentioned disadvantages, and meets the recognized need for such an invention by providing a composition and method for treating iron deficiency anemia.

According to its major aspects and broadly stated, the present invention in its preferred form is a composition comprising ionic iron(s) and/or chelated iron(s) in combination with heme iron and/or heme iron polypeptide, wherein heme iron polypeptide is preferably in the form of a proteolytic digest of bovine and/or porcine hemoglobin; however, it should be recognized that other derivations of heme iron polypeptide may be procured from the hemoglobin and/or myoglobin molecular complexes of alternate animal species. The ionic irons of the present composition are preferably in the form of soluble iron salts, but may further include, without limitation, slightly soluble iron salts and/or insoluble iron salts. Additionally, the chelated iron of the present composition may be selected from any one or more of the preferred complexes of iron polysaccharide, iron bis glycinate, and/or iron proteinate; although alternate chelated iron complexes are contemplated. In certain embodiments, the present composition further comprises vitamins and minerals, including, without limitation, folic acid, vitamin A, vitamin B (all series), vitamin C, vitamin D, vitamin E, calcium, magnesium, or the like, so as to provide a prenatal composition.

More specifically, the composition of the present invention may comprise any combination of the following amounts of the specific ingredients (nota bene: all of the following amounts of iron are in terms of total elemental iron): heme iron or heme iron polypeptide, or a combination thereof, in an amount between about 2 mg and about 12 mg, and preferably between about 6 mg and about 9 mg; and, ionic iron(s) or chelated iron(s), or a combination thereof, in an amount between about 15 mg and about 100 mg, and preferably between about 20 mg and about 75 mg. The composition may further specifically comprise folic acid in an amount between about 0.1 mg and about 5 mg, and preferably between about 0.4 mg and about 2 mg; and/or, vitamin B12 in an amount between about 1 mcg and about 900 mcg, and preferably between about 12 mcg and about 500 mcg.

In a preferred embodiment of the present invention, the composition comprises heme iron or heme iron polypeptide, or a combination thereof, in an amount of about 6 mg (total elemental iron); and, ionic iron(s) or chelated iron(s), or a combination thereof, in an amount of about 21 mg (total elemental iron), wherein the instant composition may further selectively comprise any one or more of the foregoing vitamins and minerals, including folic acid and/or vitamin B12 within the limits prescribed hereinabove.

In still another preferred embodiment of the present invention, the composition comprises heme iron or heme iron polypeptide, or a combination thereof, in an amount of about 12 mg (total elemental iron); and, ionic iron(s) or chelated iron(s), or a combination thereof, in an amount of about 15 mg (total elemental iron), wherein the instant composition may further selectively comprise any one or more of the foregoing vitamins and minerals, including folic acid and/or vitamin B12 within the limits prescribed hereinabove.

In yet another preferred embodiment of the present invention, the composition comprises heme iron or heme iron polypeptide, or a combination thereof, in an amount of about 12 mg (total elemental iron); and, ionic iron(s) or chelated iron(s), or a combination thereof, in an amount of about 63 mg (total elemental iron), wherein the instant composition may further selectively comprise any one or more of the foregoing vitamins and minerals, including folic acid and/or vitamin B12 within the limits prescribed hereinabove.

In other embodiments of the present invention, various compositions may comprise heme iron and/or heme iron polypeptide in combination with ionic iron(s) and/or chelated iron(s), each in any amount, within the prescribed limits described hereinabove, or otherwise selected for effective treatment and/or prevention of iron deficiency anemia. As such, via administration of effective dosages of the present composition, the instant invention further includes methods for treating and/or preventing iron deficiency anemia, and the physiological, biochemical, morphological, and behavioral manifestations symptomatic of same. Furthermore, inclusion of the foregoing prenatal vitamins within the present composition further provides an effective vitamin supplement for pregnant females, wherein other measured compositions may further be utilized for nursing mothers during periods of increased iron demand (i.e., lactational periods).

Accordingly, a feature and advantage of the present invention is its ability to provide a composition comprising heme iron and/or heme iron polypeptide in combination with ionic iron(s) and/or chelated iron(s).

Another feature and advantage of the present invention is its ability to provide a composition comprising heme iron and/or heme iron polypeptide in combination with ionic iron(s) and/or chelated iron(s), in addition to various selected prenatal vitamins.

Still another feature and advantage of the present invention is its ability to provide a composition comprising heme iron and/or heme iron polypeptide in combination with ionic iron(s) and/or chelated iron(s), for the treatment and/or prevention of iron deficiency anemia.

Yet another feature and advantage of the present invention is its ability to provide a composition comprising heme iron and/or heme iron polypeptide in combination with ionic iron(s) and/or chelated iron(s), in addition to a various selected prenatal vitamins, for the treatment and/or prevention of iron deficiency anemia.

Still yet another feature and advantage of the present invention is its ability to provide a composition comprising heme iron and/or heme iron polypeptide in combination with ionic iron(s) and/or chelated iron(s), as an effective vitamin supplement for pregnant and/or nursing females.

A further feature and advantage of the present invention is its ability to provide a composition comprising heme iron and/or heme iron polypeptide in combination with ionic iron(s) and/or chelated iron(s), in addition to a various selected vitamins, as an effective vitamin supplement for pregnant and/or nursing females.

Still a further feature and advantage of the present invention is its ability to provide methods for the treatment and/or prevention of iron deficiency anemia, by administering a composition comprising heme iron and/or heme iron polypeptide in combination with ionic iron(s) and/or chelated iron(s) and, selectively, various vitamins, prenatal or otherwise.

These and other features and advantages of the invention will become more apparent to one skilled in the art from the following description and claims when read in light of the accompanying drawings.

DETAILED DESCRIPTION OF THE PREFERRED AND SELECTED ALTERNATIVE EMBODIMENTS

In describing the preferred and selected alternate embodiments of the present invention, specific terminology is employed for the sake of clarity. The invention, however, is not intended to be limited to the specific terminology so selected, and it is to be understood that each specific element includes all technical or compositional equivalents that operate or perform in a similar manner to accomplish similar functions.

The present invention is a composition and method for treating and/or preventing iron deficiency anemia.

Iron Compositions

The composition of the present invention preferably comprises heme iron in combination with ionic iron(s) and/or chelated iron(s). In another preferred embodiment of the present invention, the composition preferably comprises heme iron polypeptide in combination with ionic iron(s) and/or chelated iron(s), wherein the heme iron polypeptide is preferably in the form of a proteolytic digest of bovine and/or porcine hemoglobin; however, it should be recognized that other derivations of heme iron polypeptide may be procured from the hemoglobin and/or myoglobin molecular complexes of alternate animal species. In still another preferred embodiment of the present invention, the composition preferably comprises heme iron and heme iron polypeptide in combination with ionic iron(s) and/or chelated iron(s). Indeed, the present invention contemplates numerous preferred embodiments of the instant composition, wherein the amounts of each specific ingredient, in any varying combination, may be appropriately selected based upon the treatment measures, protocols and/or other diagnostics relevant to the targeted patient populace. Accordingly, and as more fully described hereinbelow, the amounts and type of each specific ingredient, in any varying combination, are only exemplary preparations of the present composition and, thus, are not intended to so limit the multitude of combinations attainable from the present invention. It is also to be understood that as used in the specification and in the claims, "a" or "an" can mean one or more, depending upon the context in which it is used.

The ionic irons of the present composition are preferably in the form of soluble iron salts, but may further include, without limitation, slightly soluble iron salts, insoluble iron salts, carbonyl irons, and blends, mixtures or combinations thereof. Accordingly, the selected soluble iron salt(s) may include, without limitation, ferrous sulfate, ferrous gluconate, ferrous fumarate, ferric hypophosphite, ferric albuminate, ferric chloride, ferric citrate, ferric oxide saccharated, ferric ammonium citrate, ferrous chloride, ferrous iodide, ferrous lactate, ferric trisglycinate, ferrous bisglycinate, ferric nitrate, ferrous hydroxide saccharate, ferric sulfate, ferric gluconate, ferric aspartate, ferrous sulfate heptahydrate, ferrous phosphate, ferric ascorbate, ferrous formate, ferrous acetate, ferrous malate, ferrous glutamate, ferrous cholinisocitrate, ferroglycine sulfate, ferric oxide hydrate, ferric pyrophosphate soluble, ferric hydroxide saccharate, ferric manganese saccharate, ferric subsulfate, ferric ammonium sulfate, ferrous ammonium sulfate, ferric sesquichloride, ferric choline citrate, ferric manganese citrate, ferric quinine citrate, ferric sodium citrate, ferric sodium edetate, ferric formate, ferric ammonium oxalate, ferric potassium oxalate, ferric sodium oxalate, ferric peptonate, ferric manganese peptonate, other pharmaceutically acceptable soluble iron salts, blends, mixtures and/or combinations thereof.

As an alternative to the selected soluble iron salt(s), or in conjunction therewith, a slightly soluble salt(s) may be utilized in the present composition, wherein the slightly soluble salt(s) may include, without limitation, ferric acetate, ferric fluoride, ferric phosphate, ferric pyrophosphate, ferrous pyrophosphate, ferrous carbonate saccharated, ferrous carbonate mass, ferrous succinate, ferrous citrate, ferrous tartrate, ferric fumarate, ferric succinate, ferrous hydroxide, ferrous nitrate, ferrous carbonate, ferric sodium pyrophosphate, ferric tartrate, ferric potassium tartrate, ferric subcarbonate, ferric glycerophosphate, ferric saccarate, ferric hydroxide saccharate, ferric manganese saccharate, ferrous ammonium sulfate, other pharmaceutically acceptable slightly soluble iron salts, blends, mixtures and/or combinations thereof.

Additionally, as an alternative to the selected soluble iron salt(s) and/or slightly soluble salt(s), or in conjunction therewith, an insoluble salt(s) may be utilized in the present composition, wherein the insoluble salt(s) may include, without limitation, ferric sodium pyrophosphate, ferrous carbonate, ferric hydroxide, ferrous oxide, ferric oxyhydroxide, ferrous oxalate, other pharmaceutically acceptable insoluble iron salts, blends, mixtures and/or combinations thereof.

As described hereinabove, and as an alternative to any one or more of the foregoing enumerated iron salts, or in conjunction therewith, the present composition may selectively comprise a chelated iron in combination with the selected heme iron and/or heme iron polypeptide. Accordingly, in such an embodiment, the chelated iron of the present composition may be selected from any one or more of the preferred complexes of iron polysaccharide, iron bis glycinate, and/or iron proteinate. However, alternate chelated iron complexes are contemplated and, as such, may include, without limitation, methylidine-iron complex, EDTA-iron complex, phenanthrolene iron complex, p-toluidine iron complex, ferrous saccharate complex, ferrlecit, ferrous gluconate complex, ferrum vitis, ferrous hydroxide saccharate complex, iron-arene sandwich complexes, acetylacetone iron complex salt, iron-dextran complex, iron-dextrin complex, iron-sorbitol-citric acid complex, saccharated iron oxide, ferrous fumarate complex, iron porphyrin complex, iron phtalocyamine complex, iron cyclam complex, dithiocarboxy-iron complex, desferrioxamine-iron complex, bleomycin-iron complex, ferrozine-iron complex, iron perhaloporphyrin complex, alkylenediamine-N,N'-disuccinic acid iron(III) complex, hydroxypyridone-iron(III) complex, aminoglycoside-iron complex, transferrin-iron complex, iron thiocyanate complex, iron complex cyanides, porphyrinato iron(III) complex, polyaminopolycarbonate iron complexes, dithiocarbamate iron complex, adriamycin iron complex, anthracycline-iron complex, MGD-iron complex, ferrioxamine B, ferrous citrate complex, ferrous sulfate complex, ferric gluconate complex, ferrous succinate complex, polyglucopyranosyl iron complex, polyaminodisuccinic acid iron complex, biliverdin-iron complex, deferiprone iron complex, ferric oxyhydride-dextran complex, dinitrosyl dithiolato iron complex, iron lactoferrin complexes, 1,3-PDTA ferric complex salts, diethylenetriaminepentaacetic acid iron complex salts, cyclohexanediaminetetraacetic acid iron complex salts, methyliminodiacetic acid iron complex salts, glycol ether diaminetetraacetic acid iron complex salts, ferric hydroxypyrone complexes, ferric succinate complex, ferric chloride complex, ferric glycine sulfate complex, ferric aspartate complex, sodium ferrous gluconate complex, ferrous hydroxide polymaltose complex, other pharmaceutically acceptable chelated iron complexes, blends, mixtures and/or combinations thereof.

Still, in certain embodiments, the present composition may further selectively comprise vitamins and minerals, including, without limitation, folic acid, vitamin A, vitamin B (all series, including B3, B6, B12), vitamin C, vitamin D, vitamin E, calcium, magnesium, or the like, so as to provide a prenatal composition. Accordingly, as used herein, the term "vitamin B3" refers to niacin and nicotinic acid. As also used herein, the term "vitamin B6" refers to pyridoxal, pyridoxamine and pyridoxine compounds. The term "vitamin B12" refers to all forms of cobalamin including, without limitation, hydroxocobalamin, cyanocobalamin and methylcobalamin. The term "vitamin C" is used herein to refer to any form of vitamin C, including ascorbate and L threonate. The term "vitamin D" is used to refer to both cholecalciferol (vitamin D3) and ergocalciferol (vitamin D2). The term "vitamin E" is used herein to refer to alpha-tocopherol, d-alpha-tocopherol, d-alpha-tocopheryl succinate (or acetate), dl-alpha-tocopherol, dl-alpha-tocopheryl acetate (or succinate), gamma tocopherol, mixed tocopherols, and dl-alpha tocopherol nicotinate. The term "calcium" is used herein to refer to any form of calcium including calcium carbonate, phosphate, lactate, gluconate, citrate and combinations thereof. The term "magnesium" is used herein to refer to any form of magnesium, including magnesium oxide, magnesium chloride, magnesium lactate, magnesium sulfate and magnesium gluconate. As such, the various compositions of the present invention may include one or more forms of the foregoing vitamins and/or minerals in any amount and in any combination with the selected heme iron and/or heme iron polypeptide, and the selected iron salt(s) and/or chelated iron(s).

Turning now to one of the many preferred embodiments of the present invention, a preferred composition preferably comprises any combination of the following amounts of the specific ingredients (nota bene: all of the following amounts of iron are in terms of total elemental iron): heme iron or heme iron polypeptide, or a combination thereof, in an amount between about 2 mg and about 12 mg, and preferably between about 6 mg and about 9 mg; and, ionic iron(s) or chelated iron(s), or a combination thereof, in an amount between about 15 mg and about 100 mg, and preferably between about 20 mg and about 75 mg. The instant composition may further specifically comprise folic acid in an amount between about 0.1 mg and about 5 mg, and preferably between about 0.4 mg and about 2 mg; and/or, vitamin B12 in an amount between about 1 mcg and about 900 mcg, and preferably between about 12 mcg and about 500 mcg.

In another preferred embodiment of the present invention, the composition comprises one of heme iron, heme iron polypeptide, ionic iron(s) and chelated iron(s) in the ranges prescribed hereinabove, and the remaining selected ingredients in any amount. For example, the composition may comprises heme iron in an amount between about 2 mg and about 12 mg, and preferably between about 6 mg and about 9 mg (total elemental iron); and, ionic iron(s) or chelated iron(s), or a combination thereof, in any amount. Another composition may similarly comprise heme iron polypeptide in an amount between about 2 mg and about 12 mg, and preferably between about 6 mg and about 9 mg (total elemental iron); and, ionic iron(s) or chelated iron(s), or a combination thereof, in any amount. Another composition may comprise heme iron and heme iron polypeptide in a combined amount between about 2 mg and about 12 mg, and preferably between about 6 mg and about 9 mg (total elemental iron); and, ionic iron(s) or chelated iron(s), or a combination thereof, in any amount. Another composition may comprise ionic iron(s) in an amount between about 15 mg and about 100 mg, and preferably between about 20 mg and about 75 mg (total elemental iron); and, heme iron or heme iron polypeptide, or a combination thereof, in any amount. Another composition may comprise chelated iron(s) in an amount between about 15 mg and about 100 mg, and preferably between about 20 mg and about 75 mg (total elemental iron); and, heme iron or heme iron polypeptide, or a combination thereof, in any amount. Another composition may comprise ionic iron(s) and chelated iron(s) in a combined amount between about 15 mg and about 100 mg, and preferably between about 20 mg and about 75 mg (total elemental iron); and, heme iron or heme iron polypeptide, or a combination thereof, in any amount. Additionally, the foregoing compositions may further selectively comprise any one or more of the foregoing vitamins and minerals, including folic acid and/or vitamin B12 within the limits prescribed hereinabove, or in any amount.

In still another preferred embodiment of the present invention, the composition comprises heme iron or heme iron polypeptide, or a combination thereof, in an amount of about 6 mg (total elemental iron); and, ionic iron(s) or chelated iron(s), or a combination thereof, in an amount of about 21 mg (total elemental iron), wherein the instant composition may further selectively comprise any one or more of the foregoing vitamins and minerals, including folic acid and/or vitamin B12 within the limits prescribed hereinabove. A preferred variation of the instant embodiment comprises heme iron or heme iron polypeptide, or a combination thereof, in an amount of about 6 mg (total elemental iron); and, ionic iron(s) or chelated iron(s), or a combination thereof, in any amount. Another preferred variation of the instant embodiment comprises ionic iron(s) or chelated iron(s), or a combination thereof, in an amount of about 21 mg (total elemental iron); and, heme iron or heme iron polypeptide, or a combination thereof, in any amount.

In still yet another preferred embodiment of the present invention, the composition comprises heme iron or heme iron polypeptide, or a combination thereof, in an amount of about 12 mg (total elemental iron); and, ionic iron(s) or chelated iron(s), or a combination thereof, in an amount of about 15 mg (total elemental iron), wherein the instant composition may further selectively comprise any one or more of the foregoing vitamins and minerals, including folic acid and/or vitamin B12 within the limits prescribed hereinabove. A preferred variation of the instant embodiment comprises heme iron or heme iron polypeptide, or a combination thereof, in an amount of about 12 mg (total elemental iron); and, ionic iron(s) or chelated iron(s), or a combination thereof, in any amount. Another preferred variation of the instant embodiment comprises ionic iron(s) or chelated iron(s), or a combination thereof, in an amount of about 15 mg (total elemental iron); and, heme iron or heme iron polypeptide, or a combination thereof, in any amount.

In a further preferred embodiment of the present invention, the composition comprises heme iron or heme iron polypeptide, or a combination thereof, in an amount of about 12 mg (total elemental iron); and, ionic iron(s) or chelated iron(s), or a combination thereof, in an amount of about 63 mg (total elemental iron), wherein the instant composition may further selectively comprise any one or more of the foregoing vitamins and minerals, including folic acid and/or vitamin B12 within the limits prescribed hereinabove. A preferred variation of the instant embodiment comprises heme iron or heme iron polypeptide, or a combination thereof, in an amount of about 12 mg (total elemental iron); and, ionic iron(s) or chelated iron(s), or a combination thereof, in any amount. Another preferred variation of the instant embodiment comprises ionic iron(s) or chelated iron(s), or a combination thereof, in an amount of about 63 mg (total elemental iron); and, heme iron or heme iron polypeptide, or a combination thereof, in any amount.

In other embodiments of the present invention, various compositions may comprise heme iron and/or heme iron polypeptide in combination with ionic iron(s) and/or chelated iron(s), each in any amount, within the prescribed limits described hereinabove, or otherwise selected for effective treatment and/or prevention of iron deficiency anemia, as more fully described hereinbelow.

Auxiliary Agents

The iron compositions of the present invention may be a part of a formulation that also contains at least one of any suitable auxiliary agents such as, but not limited to, diluents, binders, stabilizers, buffers, salts, lipophilic solvents, preservatives, or the like. Pharmaceutically acceptable auxiliaries are preferred. Examples and methods of preparing such sterile solutions are well known in the art and can be found in well-known literature such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound.

Pharmaceutical excipients and additives useful in the present invention include, but are not limited to, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination in ranges of 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the present invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, sorbitol (glucitol), myoinositol and the like.

The compositions of the present invention can also be a part of a formulation that includes a buffer or a pH-adjusting agent. Typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, compositions of the invention can be a part of a formulation that includes polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, anti-static agents, surfactants (e.g., polysorbates such as "TWEEN 20" and "TWEEN 80"), lipids (e.g., phospholipids, fatty acids), steroids (e.g., cholesterol), and chelating agents (e.g., EDTA). These and additional known pharmaceutical excipients and/or additives suitable for use in the present invention are known in the art, e.g., as listed in REMINGTON: THE SCIENCE & PRACTICE OF PHARMACY ($19^{th}$ ed., Williams & Williams (1995)) and PHYSICIAN'S DESK REFERENCE ($52^{nd}$ ed., Medical Economics (1998)), the disclosures of which are expressly entirely incorporated herein by reference.

Formulations for Oral Administration

For oral administration in the form of a tablet or capsule, the various compositions described herein may be combined with an oral, non-toxic pharmaceutically acceptable inert carrier such as ethanol, glycerol, water and the like to create the formulation. Moreover, when desired or necessary, suitable binders, lubricants, disintegrating agents, flavoring and coloring agents may also be incorporated into the mixture. Suitable binders include, without limitation, starch; gelatin; natural sugars such as glucose or beta-lactose; corn sweeteners; natural and synthetic gums such as acacia, tragacanth, or sodium alginate, carboxymethylcellulose; polyethylene glycol; waxes and the like. Lubricants used in these dosage forms include, without limitation, sodium oleate, sodium stearate, calcium stearate, sodium benzoate, sodium acetate, sodium chloride and the like. Disintegrators include, without limitation, starch, methyl cellulose, agar, bentonite, xanthan gum and the like. In one embodiment, a composition or formulation suitable for oral administration could comprise carnauba wax, citric acid, dicalcium phosphate, hydroxypropyl methylcellulose, calcium stearate, microcrystalline cellulose, polyethylene glycol, polysorbate 80, riboflavin, silicon dioxide, sodium benzoate, sodium citrate, sodium starch glycolate, sorbic acid, starch, stearic acid and titanium dioxide.

Compositions or formulations of the present invention suitable for oral administration may be presented as discrete units such as capsules, cachets or tablets each containing a predetermined amount of a ingredient; as a powder or granules; as a solution or a suspension in an aqueous liquid or a nonaqueous liquid; or as an oil-in-water liquid emulsion or a water-in-oil emulsion and as a bolus, etc. In a preferred embodiment, the composition or formulation is in the form of a tablet.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the ingredient(s) therein.

Preferred unit dosage formulations are those containing a daily dose or unit, daily sub-dose, or an appropriate fraction thereof, of the administered ingredient. In a more preferred embodiment, the unit dosage formulation contains from one daily dose or half of a daily dose of the compositions described hereinabove.

EXAMPLE

Preparation of Composition for Oral Administration

A composition of the present invention was prepared that comprises weighed amounts of heme iron polypeptide, iron polysaccharide, folic acid, hydroxocobalamin, calcium silicate synthetic (Micro Cel), microcrystalline cellulose PH-200, silicon dioxide FG, modified cellulose gum (Ac-Di-Sol), and magnesium stearate NF.

All ingredients were filtered through a #20 mesh screen. Heme iron polypeptide and iron polysaccharide were pre-blended in an LV blender with calcium silicate synthetic for 10 minutes. If the blend was lumpy, it was passed through a #20 mesh screen.

Folic acid, hydroxocobalamin, a selected amount of microcrystalline cellulose, and the foregoing pre-blend were loaded into an XLV blender and blended for 15 minutes. Thereafter, silicon dioxide FG, modified cellulose gum, and the remainder of microcrystalline cellulose were loaded into the XLV blender, and all materials were blended for an additional 10 minutes. Magnesium stearate was then added, and all materials were blended for an additional 5 minutes.

Following completion of the blend process, the blend was discharged and compressed into tablets according to selected specifications. The finished tablets were coated in an Accela Cota, utilizing dispersed OPADRY white with purified water as the coating solution.

Formulations for Other Routes of Administration

Formulations suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

For parenteral administration, sterile suspensions and solutions are desired. Isotonic preparations, which generally contain suitable preservatives, are employed when intravenous administration is desired. The compositions may be administered parenterally via injection of a formulation consisting of the active ingredients dissolved in an inert liquid carrier. The term "parenteral," as used herein, includes, but is not limited to, subcutaneous injections, intravenous, intramuscular, intraperitoneal injections, or infusion techniques. Acceptable liquid carriers include, for example, vegetable oils such as peanut oil, cottonseed oil, sesame oil and the like, as well as organic solvents such as solketal, glycerol formal and the like. Dissolving or suspending the composition in the liquid carrier such that the final formulation contains from about 0.005% to about 30% by weight of the active ingredient, i.e., a composition of the present invention.

Formulations suitable for topical administration in the mouth include lozenges comprising the ingredients in a flavored basis, usually sucrose and acacia or tragacanth; pastilles comprising the composition in an inert basis such as gelatin and glycerin, or sucrose and acacia; and mouthwashes comprising the composition to be administered in a suitable liquid carrier. The liquid forms may include suitably flavored suspending or dispersing agents such as the synthetic and natural gums, for example, tragacanth, acacia, methyl-cellulose and the like.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the composition.

The compositions may also be entrapped in microcapsules prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions. REMINGTON'S PHARMACEUTICAL SCIENCES (A. Osol ed., 16th ed. (1980)).

In addition, the compositions may be incorporated into biodegradable polymers allowing for sustained release of the compound, the polymers being implanted in the vicinity of where delivery of the composition is desired, for example, within the buccal cavity. The biodegradable polymers and their uses are described, for example, in detail in Brem et al., 74 J. NEUROSURG. 441-46 (1991). Suitable examples of sustained-release compositions include semipermeable matrices of solid hydrophobic polymers containing a composition of the present invention, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acidglycolic acid copolymers such as the LUPRON DEPOT® (Tap Pharmaceuticals, Inc., Chicago, Ill.) (injectable microspheres composed of lactic acid glycolic acid copolymer and leuprolide acetate), and poly-D-(−)-3-hydroxybutyric acid.

Pharmaceutically Acceptable Preservatives

The present invention provides stable compositions as well as preserved solutions and formulations containing a preservative as well as multi-use preserved formulations suitable for pharmaceutical or veterinary use, comprising a composition disclosed herein in a pharmaceutically acceptable formulation. Formulations in accordance with the present invention may optionally contain at least one known preservative. Preservatives include, but are not limited to, phenol, m-cresol, p-cresol, o-cresol, chlorocresol, benzyl alcohol, phenylmercuric nitrite, phenoxyethanol, formaldehyde, chlorobutanol, calcium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein. Non-limiting examples include, no preservative, 0.1-2% m-cresol, 0.1-3% benzyl alcohol, 0.001-0.5% thimerosal, 0.001-2.0% pheno, 0.0005-1.0% alkylparaben(s), and the like.

Other excipients, e.g., isotonicity agents, buffers, antioxidants, preservative enhancers, can be optionally added to the diluent. An isotonicity agent such as glycerin is commonly used at known concentrations. A physiologically tolerated buffer is preferably added to provide improved pH control. The formulations can cover a wide range of pHs, such as from about pH 4.0 to about pH 10.0, specifically, a range from about pH 5.0 to about pH 9.0, and more specifically, a range of about 6.0 to about 8.0. Suitable buffers include phosphate buffers, for example, sodium phosphate and phosphate buffered saline (PBS).

Method for Treating Iron Deficiency

As described hereinabove, compositions of the present invention may comprise heme iron and/or heme iron polypeptide in combination with ionic iron(s) and/or chelated iron(s), each in any amount, within the prescribed limits described hereinabove, or otherwise selected for effective treatment and/or prevention of iron deficiency anemia. As such, via administration of effective dosages of the present composition, the instant invention further includes methods for treating and/or preventing iron deficiency anemia, and the physiological, biochemical, morphological, and behavioral manifestations symptomatic of same. Furthermore, inclusion of the foregoing prenatal vitamins within the present composition further provides an effective vitamin supplement for pregnant females, wherein other measured compositions may further be utilized for nursing mothers during periods of increased iron demand (i.e., lactational periods). Still other compositions may be prepared specifically for administration to children.

As used herein, the term "treatment of" or "treating" a condition does not require elimination of the condition, i.e., curing of a disease. Therefore, an "effective amount" or "effective dosage" of the present composition is defined herein as an amount of the composition capable of preventing or reducing the occurrence or severity of iron deficiency anemia, and/or the physiological, biochemical, morphological, and behavioral manifestations symptomatic of same.

Accordingly, implementation of the present method preferably comprises administration of a composition comprising any combination of the following amounts of the specific ingredients ("mg" amount representative of total elemental iron): heme iron or heme iron polypeptide, or a combination thereof, in an amount between about 2 mg and about 12 mg, and preferably between about 6 mg and about 9 mg; and, ionic iron(s) or chelated iron(s), or a combination thereof, in an amount between about 15 mg and about 100 mg, and preferably between about 20 mg and about 75 mg. The composition may further specifically comprise folic acid in an amount between about 0.1 mg and about 5 mg, and preferably between about 0.4 mg and about 2 mg; and/or, vitamin B12 in an amount between about 1 mcg and about 900 mcg, and preferably between about 12 mcg and about 500 mcg.

Although the present invention contemplates treatment and/or prevention of iron deficiency anemia, it should be recognized that the present composition and method may be utilized to treat and/or prevent other forms or manifestations of iron deficiency, wherein methods of treatment of such alternate and additional manifestations may include administering a composition according any of the foregoing descriptions, or, alternatively, compositions comprising any of the afore-described ingredients in any selected combination.

Routes of Administration

When treating a condition associated with iron deficiency, the compositions disclosed herein may be administered to an individual by any of the following routes: oral, parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, and transdermal means. In a preferred embodiment, the present compositions are administered orally.

Having thus described the preferred and selected alternate embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

What is claimed is:

1. A pharmaceutical composition for treating iron deficiency or iron deficiency anemia in a human, consisting essentially of:
    heme iron polypeptide; and,
    at least one chelated iron selected from the group consisting of iron polysaccharide, iron bisglycinate, and iron proteinate, and combinations thereof,
    wherein said pharmaceutical composition is formulated for oral administration, and is contained within a unit selected from the group consisting of a tablet and a capsule.

2. A pharmaceutical composition for treating iron deficiency or iron deficiency anemia in a human, consisting essentially of:
    heme iron polypeptide; and,
    iron polysaccharide,
    wherein said pharmaceutical composition is formulated for oral administration, and is contained within a unit selected from the group consisting of a tablet and a capsule.

3. A pharmaceutical composition for treating iron deficiency or iron deficiency anemia in a human, consisting essentially of:
    heme iron polypeptide;
    iron polysaccharide; and,
    at least one vitamin selected from the group consisting of folic acid, vitamin B6, vitamin B12, and combinations thereof,
    wherein said pharmaceutical composition is formulated for oral administration, and is contained within a unit selected from the group consisting of a tablet and a capsule.

4. A pharmaceutical composition for treating iron deficiency or iron deficiency anemia in a human, consisting essentially of:
    heme iron polypeptide;
    at least one chelated iron selected from the group consisting of iron polysaccharide, iron bisglycinate, and iron proteinate, and combinations thereof; and,
    at least one vitamin selected from the group consisting of folic acid, vitamin B6, vitamin B12, and combinations thereof,
    wherein said pharmaceutical composition is formulated for oral administration, and is contained within a unit selected from the group consisting of a tablet and a capsule.

5. A pharmaceutical composition for nutritional supplementation in a prenatal or lactating human female, consisting essentially of:
    heme iron polypeptide;
    iron polysaccharide; and,
    at least one nutrient selected from the group consisting of vitamins, minerals, and a combination thereof,
    wherein said pharmaceutical composition is formulated for oral administration, and is contained within a unit selected from the group consisting of a tablet and a capsule.

6. A pharmaceutical composition for nutritional supplementation in a prenatal or lactating human female, consisting essentially of:
    heme iron polypeptide;
    at least one chelated iron selected from the group consisting of iron polysaccharide, iron bisglycinate, and iron proteinate, and combinations thereof; and,
    at least one nutrient selected from the group consisting of vitamins, minerals, and a combination thereof,
    wherein said pharmaceutical composition is formulated for oral administration, and is contained within a unit selected from the group consisting of a tablet and a capsule.

7. A pharmaceutical composition for nutritional supplementation in a prenatal or lactating human female, consisting essentially of:
   heme iron polypeptide; and,
   iron polysaccharide,
   wherein said pharmaceutical composition is formulated for oral administration, and is contained within a capsule, said capsule further including additional nutrients for the prenatal or lactating human female.

8. A pharmaceutical composition for nutritional supplementation in a prenatal or lactating human female, consisting essentially of:
   heme iron polypeptide; and,
   at least one chelated iron selected from the group consisting of iron polysaccharide, iron bisglycinate, and iron proteinate, and combinations thereof;
   wherein said pharmaceutical composition is formulated for oral administration, and is contained within a capsule, said capsule further including additional nutrients for the prenatal or lactating human female.

* * * * *

UNITED STATES PATENT AND TRADEMARK OFFICE
CERTIFICATE OF CORRECTION

PATENT NO. : 8,080,520 B2
APPLICATION NO. : 12/506139
DATED : December 20, 2011
INVENTOR(S) : Venkataraman et al.

It is certified that error appears in the above-identified patent and that said Letters Patent is hereby corrected as shown below:

Col. 13, Line 66: "iron bisglycinate, and iron" should read --iron bisglycinate, iron--

Col. 14, Line 33: "iron bisglycinate, and iron" should read --iron bisglycinate, iron--

Col. 14, Line 60: "iron bisglycinate, and iron" should read --iron bisglycinate, iron--

Col. 16, Line 4: "iron bisglycinate, and iron" should read --iron bisglycinate, iron--

Signed and Sealed this
Tenth Day of July, 2012

David J. Kappos
*Director of the United States Patent and Trademark Office*